United States Patent [19]
Biscegli

[11] Patent Number: 6,004,511
[45] Date of Patent: Dec. 21, 1999

[54] HOLLOW FIBER OXYGENATOR

[75] Inventor: José Biscegli, Sao Paulo-SP, Brazil

[73] Assignee: Baxter International Inc., Deerfield, Ill.

[21] Appl. No.: 09/029,646

[22] PCT Filed: Aug. 29, 1996

[86] PCT No.: PCT/US96/14148

§ 371 Date: Jun. 17, 1998

§ 102(e) Date: Jun. 17, 1998

[87] PCT Pub. No.: WO97/08933

PCT Pub. Date: Mar. 13, 1997

[30] Foreign Application Priority Data

Sep. 1, 1995 [DE] Germany .......................... 195 32 365

[51] Int. Cl.$^6$ ........................................ A61M 1/14
[52] U.S. Cl. ................. 422/45; 422/44; 422/46
[58] Field of Search ................. 422/44, 45, 46

[56] References Cited

U.S. PATENT DOCUMENTS

| | | |
|---|---|---|
| 3,422,008 | 1/1969 | McLain . |
| 3,794,468 | 2/1974 | Leonard . |
| 4,031,012 | 6/1977 | Gics . |
| 4,038,190 | 7/1977 | Baudet et al. . |
| 4,141,835 | 2/1979 | Schael et al. . |
| 4,239,729 | 12/1980 | Hasegawa et al. . |
| 4,242,203 | 12/1980 | Amicel et al. . |
| 4,289,623 | 9/1981 | Lee .......................................... 210/247 |
| 4,407,777 | 10/1983 | Wilkinson et al. ....................... 422/46 |
| 5,143,312 | 9/1992 | Baurmeister . |
| 5,217,689 | 6/1993 | Raible ...................................... 422/46 |
| 5,234,591 | 8/1993 | Darnell et al. ...................... 210/321.81 |
| 5,236,586 | 8/1993 | Antoni et al. ......................... 210/321.8 |
| 5,733,398 | 3/1998 | Carson et al. ............................. 156/69 |
| 5,830,370 | 11/1998 | Maloney et al. ........................ 210/780 |

FOREIGN PATENT DOCUMENTS

| | | |
|---|---|---|
| 93677 | 3/1983 | European Pat. Off. . |
| 0 089 122 | 9/1983 | European Pat. Off. . |
| 0 187 708 | 8/1992 | European Pat. Off. . |
| 1470075 | 4/1977 | United Kingdom . |
| 1481064 | 7/1977 | United Kingdom . |
| 1500945 | 5/1978 | United Kingdom . |

*Primary Examiner*—Corrine McDermott
*Assistant Examiner*—Cheryl L. Huseman
*Attorney, Agent, or Firm*—Guy Cumberbatch; Lena I. Vinitskaya

[57] ABSTRACT

A hollow fiber oxygenator includes a housing defining a blood chamber between an inner core wall and an outer wall. The chamber includes at least one blood inlet and at least one blood outlet. A plurality of hollow semi-permeable fibers extend through the chamber. Each fiber has an open inlet and and an open outlet end, the ends being sealed from the chamber by sealings. The oxygenator further includes a gas inlet on one end of the chamber in communication with the inlet ends of the fibers, and a gas outlet on the other end of the chamber in communication with the outlet ends of the fibers. Blood flows into the chamber and across the exterior surfaces of the fibers to effectuate gas transfer therebetween. A partitioning wall divides the chamber into at least two sections. In one of the sections, the blood flow is co-current with the gas flow, while in another section the blood flow is counter-current with respect to the gas flow. The chamber may be annular and the partitioning wall tubular, with a first section being concentrically disposed within a second section. Desirably, blood flows in the first section counter-current with respect to the gas flow, across a flow passage way, and flows in the second section co-current with respect to the gas flow. The hollow fibers may be provided in layers with the fibers in each layer being parallel, and the fibers in adjacent layers being angled with respect to each other and with respect to the axis of the housing.

29 Claims, 5 Drawing Sheets

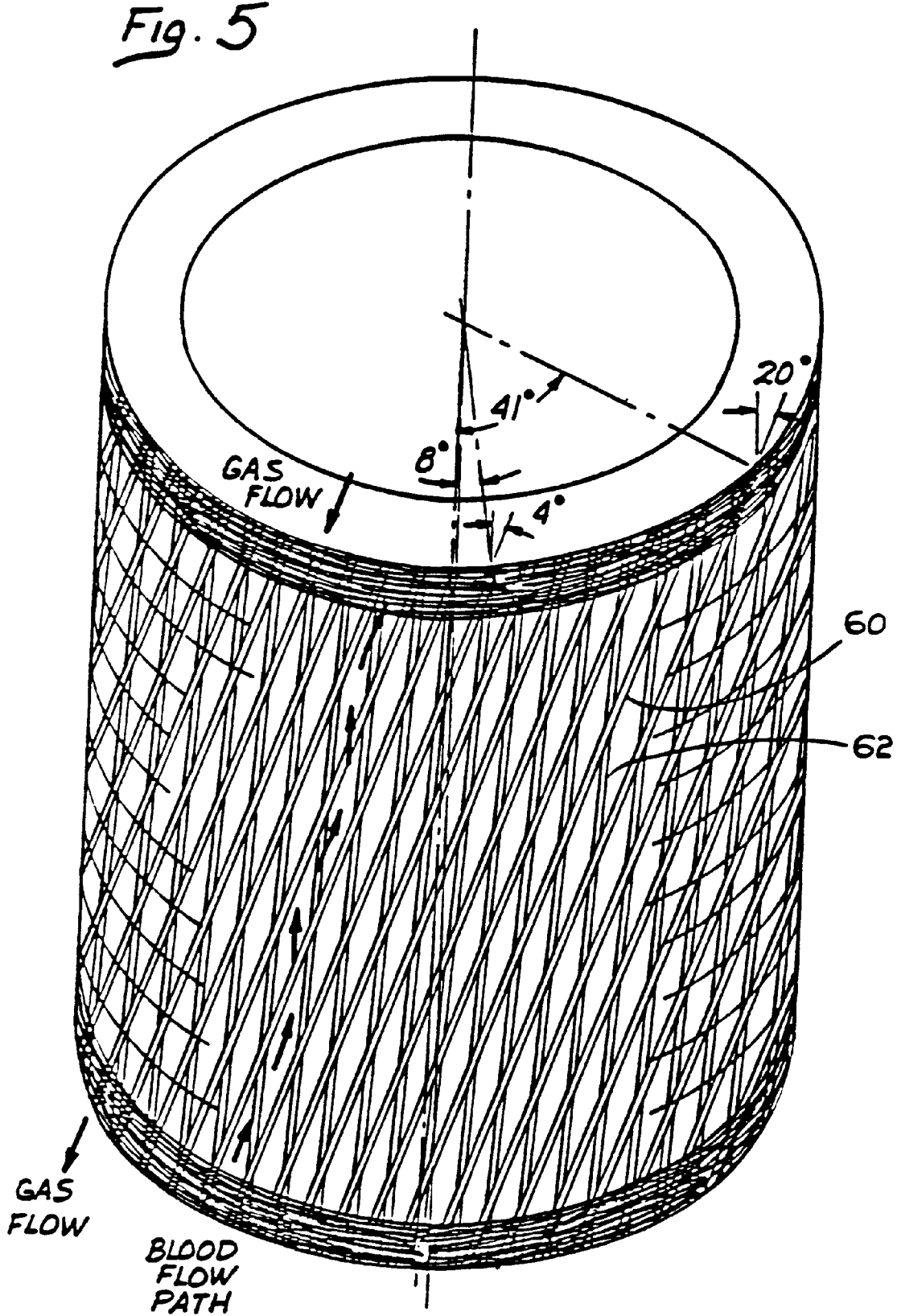

HOLLOW FIBER OXYGENATOR

FIELD OF THE INVENTION

The present invention relates to a hollow fiber oxygenator, a specific hollow fiber arrangement and a method for oxygenating blood.

BACKGROUND OF THE INVENTION

In the field of cardiopulmonary surgery which often involves an extracorporeal blood circulation, there is a demand for blood oxygenators to replace the breathing function of the lungs by removing carbon dioxide from the blood and feeding oxygen to the blood. The extracorporeal blood circulation is required to replace all functions of the patient's heart and blood circulation system, thus fulfilling its special requirements as to blood flow, blood temperature, exchange of carbon dioxide and oxygen. The physiological properties of the blood shall not be altered in the extracorporeal blood circulation system. Various blood oxygenators for use in cardiopulmonary surgery are known.

EP-A-0 089 122 discloses a hollow fiber blood oxygenator having a mat of a plurality of contiguous fiber layers around a porous core, wherein contiguous fiber mat layers exhibit an angle of divergence from the longitudinal axis of the core, wherein the sense of divergence changes in every layer. The blood flows radially across the fiber mat. The fibers do not substantially fill the whole of an annular chamber around the core.

EP-B-0 187 708 discloses a hollow fiber blood oxygenator, wherein fibers or small fiber ribbons are wound helically around a core, wherein a first plurality of fibers is wound in one sense and a second plurality of fibers is wound in the other sense similar to a yarn winding operation. The blood flows axially through the fiber windings, which occupy substantially all of an annular chamber around the core. Gas flow and blood flow may be counter-current.

U.S. Pat. No. 4,239,729 discloses a hollow fiber blood oxygenator, wherein fibers are arranged axially in an elongated housing and do not substantially fill the housing. Blood flows through the fibers whereas the oxygenating gas flows radially with respect to the fibers.

U.S. Pat. No. 3,422,008 discloses a hollow fiber blood oxygenator and a method for forming it, wherein hollow fibers are helically wound on the core in such a way that intermediate helical windings are reversed. Thus, successive layers have opposite winding sense with respect to the, core axis. The blood flow is radial. The annular space is not substantially filled with the fibers.

U.S. Pat. No. 4,031,012 discloses a separatory apparatus which can be used as an oxygenator comprising a card-shaped core on which hollow fibers are wound either parallel to the core, having an angle to the core axis, or having a cries-cross arrangement or zigzag arrangement with respect to successive layers in which the angle is reversed. A counter-current flow of blood and oxygen is preferred, wherein the blood flows outside the hollow fibers.

GB-1 481 064 discloses a membrane apparatus which may be an oxygenator having hollow fiber bundles being contained in a receptacle but not substantially filling it. An angle of 10 to 40° may be formed between adjacent layers of fiber bundles. The fluid flow is principally radial.

U.S. Pat. No. 4,141,835 discloses a dialysis apparatus, wherein a number of separated fibers are arranged in a straight line in a housing. The housing is not filled with the fibers which may also be arranged in helical lines. A fluid flows axially outside the fibers.

EP-A-0 093 677 discloses an apparatus which can be used as an oxygenator in which rolled mats of fibers are arranged, in which the fibers may be crossed in an angle between 1 and 5°. The blood flows in the fibers.

The known hollow fiber oxygenators exhibit a number of disadvantages depending on their construction. They are bulky, have a short blood flow path through the oxygenator and have, thus, a small contact zone for the blood and the gas and consequently a short residence time for the blood in the oxygenator which leads to a poor gas exchange rate. Blood and gas pressure drops may occur as well as channeling of blood or stagnation of blood in certain areas of the contact zone between blood and gas.

SUMMARY OF THE INVENTION

It is thus one object of the invention to provide a blood oxygenator of a small construction size but retaining a high gas exchange rate.

A further object of this invention is to provide a blood oxygenator which is of simple construction, allowing in particular a simple arrangement on and application to a core of hollow fibers.

A further object of this invention is to provide a blood oxygenator allowing an improved contact of blood and gas.

A further object of this invention is to provide a blood oxygenator in which the channeling of blood and areas of blood stagnation are avoided.

Still a further object of the present invention is to provide a blood oxygenator which exhibits a low pressure drop of the blood flowing through the oxygenator.

These and other objects, advantages, details, features and embodiments of this invention will become apparent to those skilled in the art from the following detailed description of the invention, the appended claims, the drawings, and the examples.

In accordance with this invention a hollow fiber oxygenator is provided, which comprises a housing, comprising a core wall and an outer wall spaced from the core wall thus forming a chamber between the walls, at least one blood inlet to and at least one blood outlet from said chamber, first and second caps closing the chamber at a first and, respectively, a second end thereof, one of the caps having at least one gas inlet, the other having at least one gas outlet associated therewith, selectively permeable continuous hollow fiber filaments extending inside the chamber between the first cap and the second cap, wherein the ends of the fibers are sealed between the core wall and the outer wall at the ends of the chamber spaced from the caps, thus leaving a header space between the sealings and the caps, the ends of the fibers being open, wherein the circumferential angle difference for the fibers between the two sealings is between 0° and 180°.

In a preferred embodiment, the fibers are arranged in a first plurality of fibers and in a second plurality of fibers, wherein the first plurality of the fibers and the second plurality of the fibers have the same directional sense but different circumferential angle differences, the length of the fibers of the first plurality of fibers being different from the length of the fibers of the second plurality of fibers.

In prior art devices the fibers have been wound around the core in a technique similar to winding yarn on a bobbin (continuous rotation of the core coupled with oscillating axial movement of the fiber guide also known as cross winding). Thereby the circumferential angle difference of a given fiber between the two sealings was always well above 360°, frequently involved several full rotations, i.e. multiples of 360°. This prior art procedure had the disadvantage that a wrapping process and thus very long fibers between the sealings was required. The present invention avoids this drawback and allows the use of much shorter fibers as well as a simpler production of the oxygenator.

Furthermore in accordance with this invention a hollow fiber oxygenator is provided, which comprises a housing, comprising a core wall and an outer wall spaced from the core wall thus forming a chamber between the walls, least one blood inlet to and at least one blood outlet from said chamber, first and second caps closing the chamber at a first and, respectively, a second end thereof, one of the caps having at least one gas inlet, the other having at least one gas outlet associated therewith, selectively permeable continuous hollow fiber filaments extending inside the chamber between the first cap and the second cap, wherein the ends of the fibers are sealed between the core wall and the outer wall at the ends of the chamber spaced from the caps, thus leaving a header space between the sealings and the caps, the ends of the fibers being open, wherein at least one partitioning wall is located between the core wall and the outer wall spaced therefrom, extending from one of the sealings towards the other sealing, thus dividing the chamber into sections, having a flow connection between the sections in the vicinity of the other sealing, allowing for counter-current flow of blood and gas in one section and co-current flow of blood and gas in another section.

By the specific arrangement of the fibers and/or the partitioning wall the residence time of the blood inside the oxygenator is increased, thereby improving the gas exchange rate of the oxygenator. By the specific orientation of the fibers inside the oxygenator a longer flow path of the blood is achieved which results in a better gas transfer, a longer residence time and thus a smaller construction size of the whole oxygenator arrangement while retaining the same performance or even improved performance. With the specific arrangement of the fibers and the blood flow path through the oxygenator no channeling of blood occurs, areas of blood stagnation are avoided and the pressure drop for the blood is rather low, thus allowing a treatment of the blood under moderate conditions which prevent or reduce the damage of the components of the blood. The specific arrangement of fibers allows a very simple construction of the blood oxygenator, especially a very simple arrangement of the fibers around the core of the oxygenator.

BRIEF DESCRIPTION OF THE DRAWINGS

Preferred embodiments of this invention will be described with reference to the drawings in which:

FIG. 5 is a perspective view of a hollow fiber arrangement according to the present invention showing the blood flow path through the fiber filaments and gives an illustration of the definitions of fiber directions.

DESCRIPTION OF THE PREFERRED EMBODIMENTS

Housing

Figure 1:
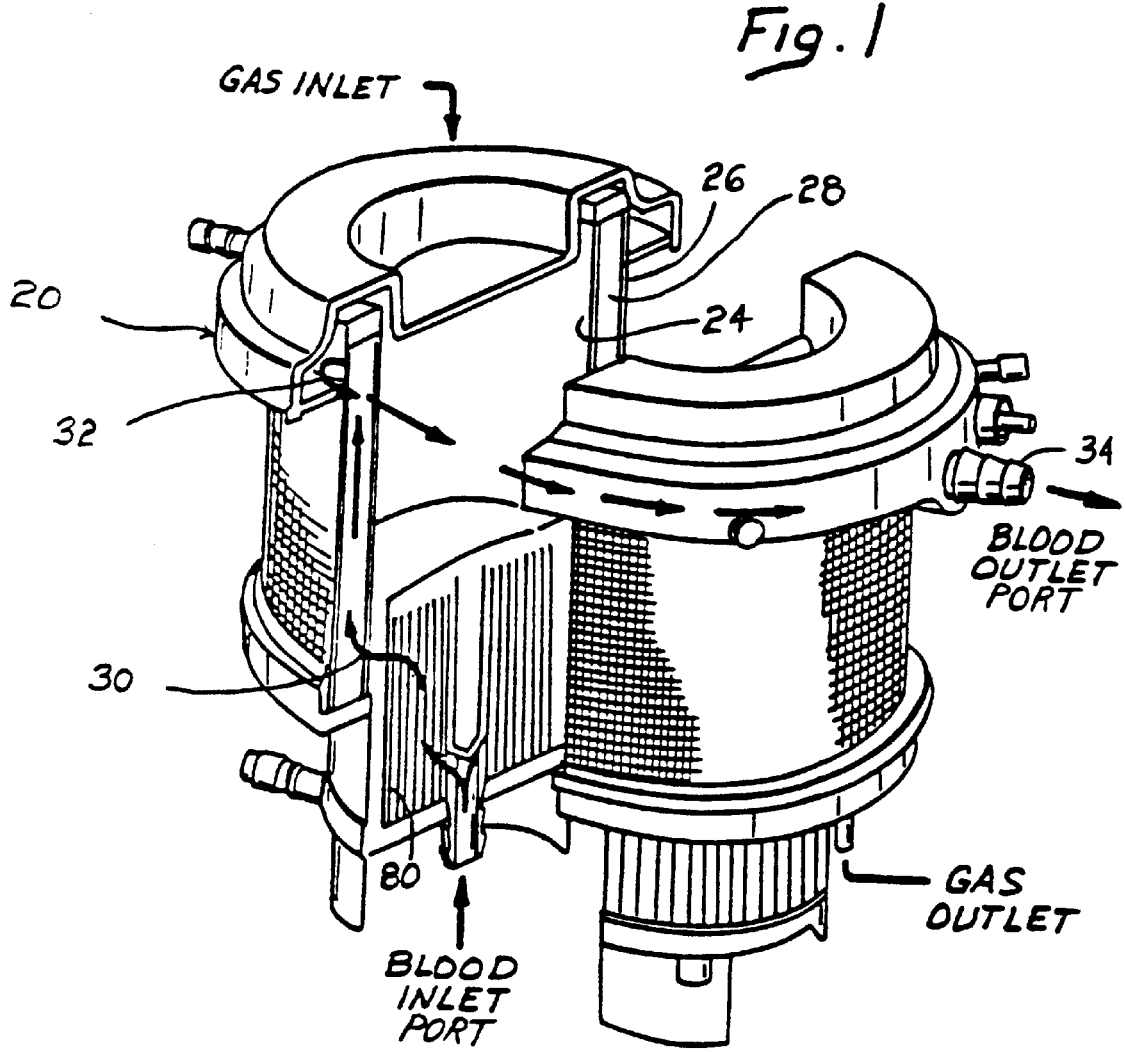
FIG. 1 is a perspective view of an assembled oxygenator according to the present invention with a partly cross-sectional view.

The housing 20, 20' of the oxygenator 22, 22' according to the present invention may be formed of any suitable material which does not adversely interfere with the blood and the free oxygen containing gas, flowing through the oxygenator, respectively. Suitable materials include, but are not limited to, glass, ceramics, metals and alloys as well as polymeric materials like polycarbonate, polyesters, polyacrylates and polymethacrylates. Copolymers and mixtures of polymers are suitable as well. The preferred materials are polymeric materials and alloys thereof.

The housing 20, 20' of the oxygenator 22, 22' comprises a core wall 24, 24' which may be of any desirable shape. The core wall 24, 24' may be of cylindrical form. It may have a circular or polygonal cross-section. Preferably, the core wall 24, 24' has a cylindrical shape with a circular cross-section, the diameter being approximately equal to the height of the cylinder.

The oxygenator further comprises an outer wall 26, 26' which is spaced from the core wall 24, 24', thus forming a chamber 28, 28' between the walls. Preferably outer wall and core wall are parallel to each other leaving a space of equal width in between. Thus, the chamber 28, 28' may be annular, in particular having a circular or polygonal cross section. In the preferred embodiment the outer wall 26, 26' forms a cylinder of circular cross-section surrounding the core cylinder and leaving a chamber in between. In a preferred embodiment the inner core 24, 24' has an outer diameter of 100 to 104 mm and a height of 130 to 150 mm, the outer wall 26, 26' having an inner diameter of 132 to 134 mm. Thus, between the two cylinders there is an annular space with a width of 13 to 17mm.

In the walls at least one blood inlet 30, 30' to and at least one blood outlet 32, 32' from the chamber 28, 28' are formed. The blood inlet 30, 30' and the blood outlet 32, 32' may be formed in the core wall 24, 24' or in the outer wall 26, 26' or in both walls. The blood inlet and the blood outlet may be located at opposite ends of the core wall or the outer wall or at the same ends, respectively.

In the preferred embodiment as depicted in FIG. 1 the blood inlet 30 is formed in the bottom section of the core wall 24. Preferably, a plurality of blood inlets 30 are formed at the circumference of the chamber 28 or of the core wall 24 so that blood being introduced in the space between the core wall 24 and the outer wall 26 may be evenly distributed around the circumference at the bottom of the core wall.

According to the preferred embodiment depicted in FIG. 1 a blood outlet port 34 is formed at the outside of the outer wall 26 at the top thereof. Like for the blood inlet 30 a plurality of outlets 32 are located at the circumference of the chamber 28, especially of the top of the outer wall 26. Thereby the blood is removed from the space 28 between the core wall 24 and the outer wall 26 evenly distributed around the circumference of the outer wall 26. By this arrangement the blood flows principally axially through the space 28 between the core wall 24 and the outer wall 26.

According to another preferred embodiment the blood inlet and the blood outlet may be respectively located at the same ends of the core wall and the outer wall.

Figure 2:
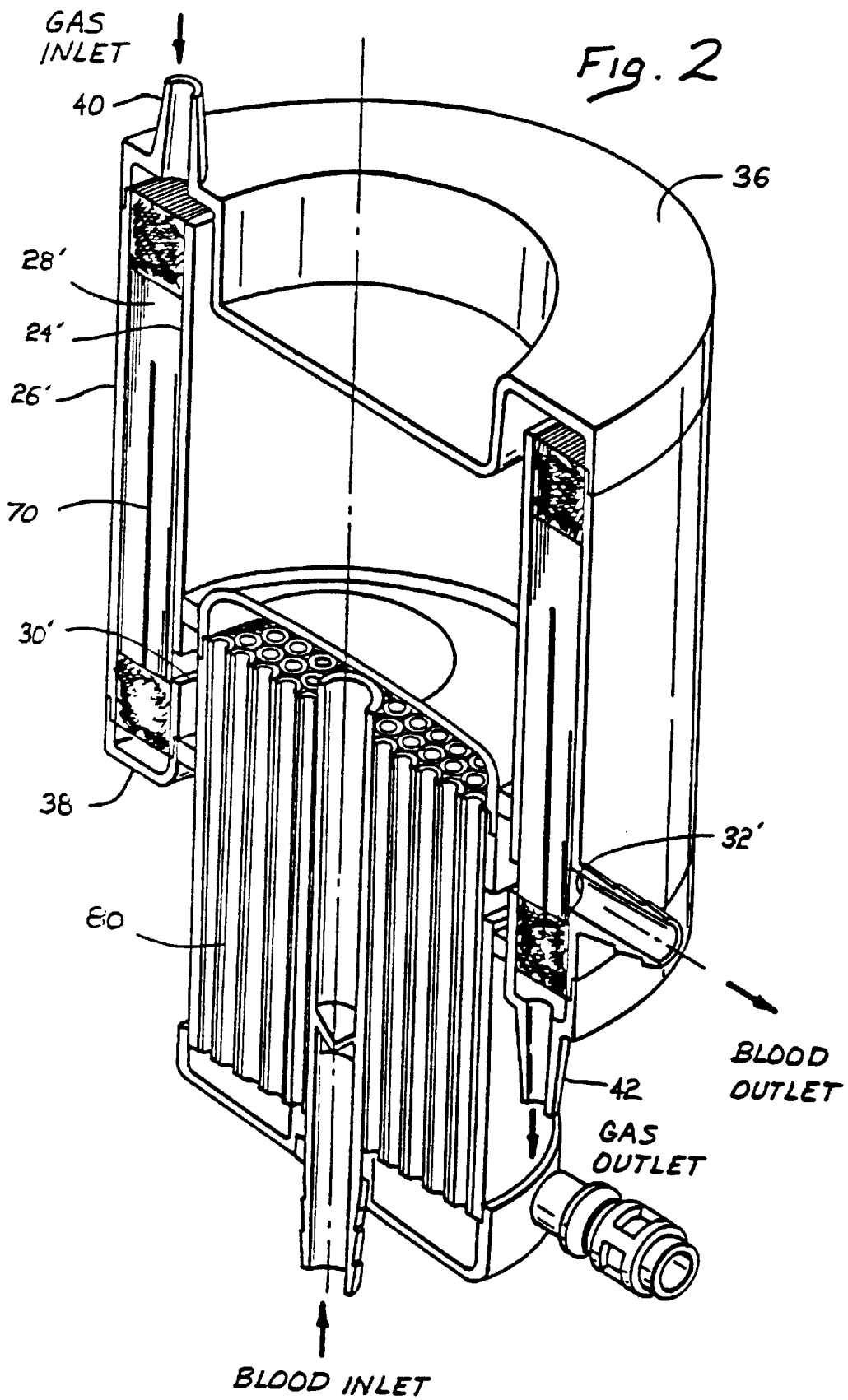
FIG. 2 is a perspective view of a second preferred embodiment of an assembled oxygenator according to the present invention with a partly cross sectional view.
Figure 3:
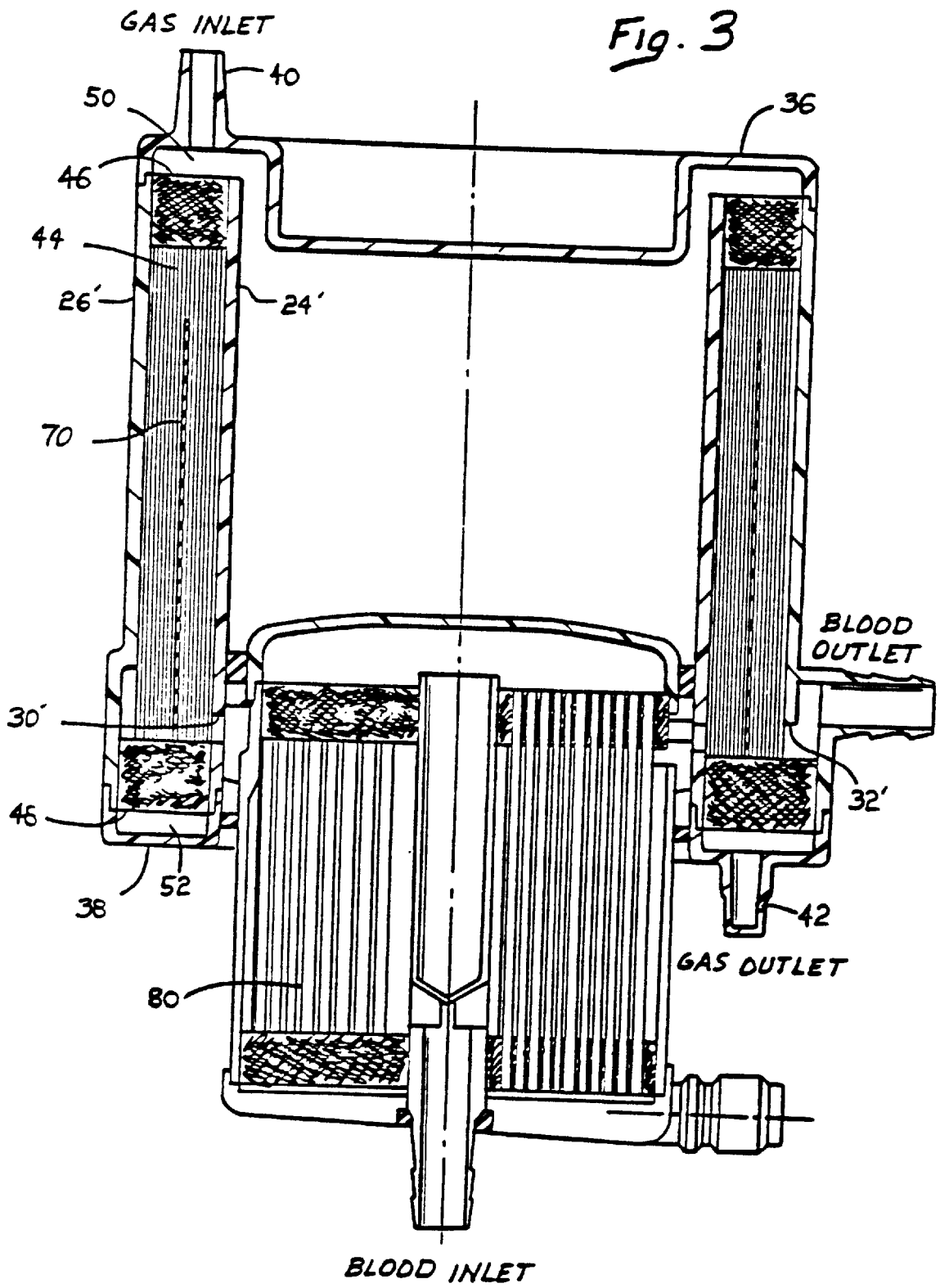
FIG. 3 is a cross-sectional view of a second preferred embodiment of the oxygenator according to the present invention of FIG. 2.

In the preferred embodiment depicted in FIGS. 2 and 3 the blood outlets 32' are arranged in the same manner as in the embodiment of FIG. 1 with the difference that the outlets are located at the bottom of the outer wall 26'.

The chamber 28' formed between the core wall 24' and the outer wall 26' is closed by first and second caps 36, 38 at a first and, respectively, a second end thereof. The caps 36, 38 may be integrally formed in the core wall 24' and the outer wall 26' but may as well be formed separately and joined to the core wall and the outer wall at a later stage.

In the caps 36, 38 there are at least one gas inlet 40 and at least one gas outlet 42 formed which may be connected with tubings for feeding and withdrawing a gas, preferably a free oxygen containing gas. In the preferred embodiment in FIGS. 2 and 3 the gas inlet 40 is formed in the top cap 36 and the gas outlet 42 is formed in the bottom cap 38.

Apart from the gas inlet, the gas outlet, the blood inlet, and the blood outlet, further connections may be provided in the core wall, the outer wall, or the caps in order to introduce e.g. means for measuring the temperature of the blood or to withdraw blood test samples.

Hollow Fibers

The hollow fibers or hollow fiber filaments used in this invention ma be any fibers that are selectively permeable and have continuous lumen therethrough.

The fibers are preferably made of polypropylene which has been modified by silicones or other types of polymers.

The hollow fiber filaments may have any desirable diameter, with an outer diameter of from 365 to 400 $\mu$m preferred, from 365 to 380 $\mu$m being especially preferred. Useful hollow fiber filaments are commercially available from AKZO and CELANESE companies and under the name oxiphan and celgard, respectively.

Another preferred hollow fiber is a microporous polypropylene hollow fiber with an inner diameter of 50 $\mu$m, an external diameter of 280 $\mu$m, an average pore size of 0,04 $\mu$m and a porosity of 50%.

Hollow Fiber Arrangement

In the embodiment of FIG. 3, the selectively permeable continuous hollow fiber filaments 44 extend inside the chamber 28' between the first cap 36 and the second cap 38. In a preferred embodiment the hollow fibers 44 substantially fill the chamber 28' between the core wall 24' and the outer wall 26'.

The ends of the fibers 44 are sealed between the core wall 24' and the outer wall 26' at the ends 46, 48 of the chamber spaced from the caps 36, 38, thus leaving a header space 50, 52 between the sealings 46, 48 and the caps. The ends of the fibers 44 are open, so that gas may flow from the gas inlet 40 of one of the caps through the fibers and finally through the gas outlet 42 in the other cap.

In the preferred embodiment depicted in FIG. 1 the fibers are arranged in the chamber in such a way that the circumferential angle difference for the fibers between the two sealings is between 0° and 180°. The term "circumferential angle difference" describes the angle through which the core must be turned around its longitudinal axis in order to arrive from one sealing of the hollow fiber to the other sealing of the hollow fiber. It may also be described as the angle between the projections of the longitudinal axis of the core, the first sealing point of the fiber and the second sealing point of the fiber into a plane which is perpendicular to the longitudinal axis of the core. FIG. 5 illustrates the term "circumferential angle difference", which is the included angle 41°.

This circumferential angle difference is between 0° and 180° for the fibers, preferably between 0° and 90°.

Figure 4:
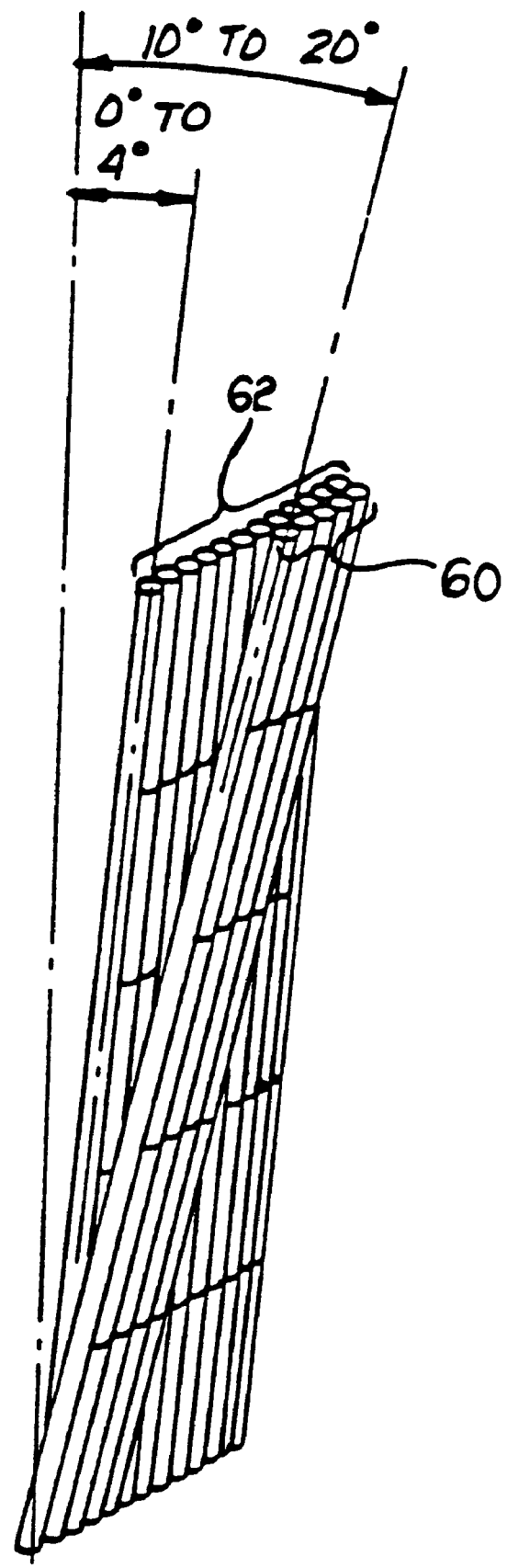
FIG. 4 is a perspective view of a hollow fiber arrangement according to the present invention.

As seen in the detail of FIG. 4, the hollow fibers are divided into a first plurality of fibers 60 and a second plurality of fibers 62. Both pluralities of fibers have the same directional sense with respect to the circumferential angle difference formed by them, but they have different circumferential angle differences. This means that the path of one of the pluralities of fibers from one sealing to the other sealing is steeper than the path of the other plurality of fibers.

Furthermore, the length of the fibers of the first plurality of fibers 60 is different from the length of the fibers of the second plurality of fibers 62. This is a result of the path of one of the plurality of fibers being steeper than the path of the other plurality of fibers. Thus, one plurality of fibers has a longer path from one sealing to the other sealing thus forming a different length of this plurality of fibers from the other plurality of fibers. Preferably, the filaments in each of the plurality of fibers are parallel to each other and pass from one sealing to the other sealing substantially without any additional curves or bends. In this way the steeper plurality of fibers necessarily has a smaller length between the sealings than the less steep plurality of fibers.

With a circumferential angle difference of 0° the fiber filaments extend principally parallel to the longitudinal axis of the core from one sealing to the other sealing. With a circumferential angle difference of 180° the fibers pass halfway around the core on their way from one sealing to the other sealing. Thus, none of the fibers passes more than halfway around the core of the oxygenator chamber.

In the oxygenators according to the state of the art usually a plurality of fibers is wound around the core in a helical fashion. At the end of the core the winding direction is reversed but the winding sense is maintained. Thus, the winding of the fibers on the core is similar to a yarn winding operation wherein the yarn is passed up and down on the turning core on which it is wound. This manner of winding fibers around the core has several restrictions: each fiber must be wound around the core several times in order to fix it to the core. Thus, usually the circumferential angle difference for the fibers between the sealings is a multiple of 360°. This large circumferential angle difference is necessary to fix the fibers on the core when the winding direction of the fiber is reversed at the end of the core. Otherwise, the fibers would fall off the core. The reversal of the winding direction but not of the winding sense leads necessarily to an arrangement of fibers in which (after cutting the fibers in the region of the sealings) one plurality of the fibers has one directional sense on the core and one circumferential angle difference and a second plurality of fibers has the opposite directional sense around the core and the same circumferential angle difference but in the opposite directional sense.

Consequently it is not possible to arrange fibers around the core with a circumferential angle difference being less than 180° (for practical reasons not less than at least several hundred degrees). Furthermore, it is not possible that two pluralities of fibers have the same directional sense but different circumferential angle differences since the arrangement of the second plurality of fibers is just the reversed arrangement of the first plurality of fibers, thus always leading to the same circumferential angle difference but different directional senses.

As a consequence the hollow fiber arrangement according to the first embodiment of the present invention cannot be obtained by rotating the core and winding the filaments from a continuous roll of filaments onto the core by reversing the feed direction of the filament at the top and bottom ends of the core, since this process for manufacturing the fiber mat is only applicable when the second plurality of the fibers are wound in the other sense with respect to the first plurality. In a preferred embodiment of the present invention the circumferential angle differences of the first plurality of fibers 60 and the second plurality of fibers 62 differ by at least 5°.

The direction of the fibers around the core may be further described by the inclination angle between the fiber filaments and the longitudinal axis of the core. If this inclination angle amounts to 0°, the fiber filaments are principally parallel to the longitudinal axis of the core. When this angle is 90°, the fibers run around the core in one plane each with which is perpendicular to the longitudinal axis of the core. According to a first embodiment of the present invention the preferably parallel fibers of the first plurality of fibers 60 have an inclination angle with the longitudinal axis of the core of less than 90° and the preferably parallel fibers of the second plurality of fibers 62 have an inclination angle with the longitudinal axis of the core of between 0° and the inclination angle of the fibers of the first plurality of fibers. Thus, the two pluralities of fibers have different inclination angles with respect to the longitudinal axis of the core. This is shown in FIG. 4 in the inclination angles of 20° and 4°.

Preferably the fibers of the first plurality of fibers 60 have an inclination angle with the longitudinal axis of the core of from 10° to 40° and the fibers of the second plurality of fibers 62 have an inclination angle with the longitudinal axis of the core of between 0° and the inclination angle of the fibers of the first plurality of fibers. In a further preferred embodiment the fibers of the first plurality of fibers 60 have an inclination angle of from 10° to 25°, especially 10° to 20°, and the fibers of the second plurality of fibers 62 have an inclination angle of from 0° to 7°, preferably 0° to 4°, more preferably 2° to 4°. In an especially preferred embodiment, the pluralities of fibers have an inclination angle of 12° and 4°, respectively.

The hollow fiber filament filling of the chamber may be achieved by arranging continuous strips of layers of fiber filaments around the core with the proviso that the axial width of said strips is longer than the axial distance between the sealings. Thus, continuous strips of layers of fiber filaments are formed and then these strips are in a second step arranged around the core, e.g. by spirally winding the continuous strip around the core. Since the axial width of the strips is longer than the axial distance between the sealings, the continuous strip need not be wound helically around the core which would involve passing the feed of the continuous strips along the longitudinal axis of the core. Thus, the arrangement of the continuous strips of layers of fiber filaments is much simpler in comparison to the yarn spool-like winding of the fibers according to the state of the art.

According to a preferred embodiment of the present invention two continuous strips of layers of fiber filaments are arranged around the core, wherein the strips have two parallel edges between which at least one layer of parallel spaced fiber filaments extends being inclined with respect to the parallel edges, wherein one strip contains the first plurality of parallel fibers with the first inclination angle and the second strip contains the second plurality of parallel fibers having the second inclination angle. The strips may have single layers of the fiber filaments and the two strips may be arranged around the core in a manner that contiguous layers of the core in radial directions have different inclination angles. This is indicated in FIG. 4.

The hollow fiber filament filling of the chamber may as well be achieved by successive layers of short single layer woven mats of the fiber filaments.

In these embodiments strips of mats of single layers of fiber filaments are prepared by first arranging a layer of long parallel fibers substantially equally spaced from each other which are then fixed in their position by a connecting element, preferably a cross thread which is a flexible small diameter monofilament. The thread must be sufficiently flexible to be easily bent around the hollow fibers. Furthermore, it must have sufficient tensile strength and tension to fix the filaments in their position, like in known tissues of clothes. This monofilament allows a regular spacing between the short single fiber filaments.

The essentially parallel fibers in each of the strips are spaced from each other by preferably 0.8 to 1.2 fiber diameters. The connecting element, preferably the thin filament-like connector or cross-thread is arranged transversely in all fibers of the strip in said strips or parallel to the upper and lower edges thereof.

In the embodiment of the present invention depicted in FIGS. 2 and 3 a known hollow fiber filament filling may be applied in which the hollow fiber filaments 44 extend inside the chamber 28' between the first cap 36 and the second cap 38. The circumferential angle difference of the fiber filaments between the sealings 46, 48 is not restricted and the directional sense of the fibers is not restricted either. However, a partitioning wall 70 described below has to be provided in this embodiment.

The hollow fiber filaments may be cross wound around the core as it is known from the prior art. This results in a first plurality of fibers being wound in one sense around the core, having one inclination angle, a second plurality of fibers being wound around the core in the opposite sense, having the opposite inclination angle. The circumferential angle differences are the same for both pluralities of fibers and this difference exceeds 360°.

Preferably the hollow fiber filaments have the arrangement described above for the first embodiment.

The hollow fibers are sealed in the space between the core wall and the outer wall at the top and the bottom thereof the ends of the filaments being open so that a gas can flow through the fiber filaments. Preferably, the fibers are sealed with a polymeric resin which has the same thermal expansion coefficient as the hollow fibers and the housing. Useful resins are polyurethane resins, wherein epoxy resins are preferred. The resin sealing of the filaments is such that a chamber is formed between the core wall, the outer wall and the resin sealings in which chamber blood can flow but not penetrate the sealings. In the preferred embodiment the sealings are arranged in such a way that between the caps and the sealings a header space is left for the introduction or removal of the free oxygen containing gas. Furthermore, the sealings are arranged in such a way that the blood inlets and blood outlets are arranged in the walls inside the chamber formed by the core wall, the outer wall and the sealings.

Partitioning Wall

According to one aspect of the present invention a partitioning wall 70 (FIG. 3) is provided between the core wall 24' and the outer wall 26' in a spaced position therefrom, which extends from one sealing 48 towards the other sealing 46, thus forming sections in the chamber 28'. The sections have a flow connection in the vicinity of the other sealing 46. The flow connection in the vicinity of the other sealing 46 may be provided in several ways. The partitioning wall 70 may extend into the other sealing 46 being sealed there and exhibiting apertures in the vicinity of this other sealing. Annular slits may be provided in this partitioning wall 70. On the other hand, the whole partitioning wall 70 may extend only to a distance from the other sealing 46 thus leaving an annular space between the end of the partitioning wall and the sealing. The size of this space or the size of the holes or annular slits may be varied depending on the flow conditions of the blood. If flow restrictions shall be imposed on the blood, the distance of holes or slits may be formed small. Preferably, the distance or slits or holes are so big that they do not affect the flow properties of the blood and do not impose a pressure drop on the blood. By this arrangement the chamber 28' is divided into sections for counter-current flow of blood and gas and co-current flow of blood and gas, respectively.

The partitioning wall 70 may be provided in each of the embodiments of the present invention, i.e. in connection with a hollow fiber filament arrangement in which the circumferential angle difference for the fibers between the sealings of the chamber is between 0° and 180°, wherein the first plurality of the fibers and the second plurality of the fibers have the same directional sense but different circumferential angle differences, the length of the fibers of the first plurality of fibers being different from the length of the fibers of the second plurality of fibers or in an arrangement in which the hollow fiber filaments extend inside the chamber between the first cap and the second cap.

Preferably, the partitioning wall is combined with the first arrangement of hollow fiber filaments. Preferably at least one partitioning wall extends from one of the sealings of the chamber to a position spaced from the other sealing of the chamber.

With respect to FIGS. 2 and 3 one partitioning wall 70 is provided in the oxygenator. The partitioning wall 70 is arranged cylindrically between the core wall 24' and the outer wall 26' and sealed in the bottom sealing 48. The partitioning wall 70 extends to a position spaced from the top sealing 46.

The partitioning wall 70 may consist of any appropriate material, e.g. sheets of polymeric material like polyethylene, polypropylene, polycarbonate or polymethacrylate. The preferred material is polycarbonate. The partitioning wall may have a thickness of from 5 to 12 $\mu$m, preferably 8 to 10 $\mu$m. The partitioning wall divides the annular chamber into two section; through which the blood is passed. The two sections of the annular chamber may have different sizes depending on the position of the partitioning wall between the core wall and the outer wall. The partitioning wall may be located in the center of the chamber, thus forming two sections of equal thickness, but depending on the desired flow properties or desired gas exchange properties the partitioning wall may be located nearer to the core wall or nearer to the outer wall. The position of the partitioning wall can affect the oxygenation results when passing blood through the chamber. By locating the partitioning wall nearer to the outer wall two sections of approximately equal volume may be obtained whereas by locating the partitioning wall in the center of the chamber two sections of different volume are obtained. The blood entering the chamber at the bottom of the core wall first flows upwardly to the top sealing of the chamber in a counter-current to the gas flow. At a position near the top sealing of the chamber the flow direction of the blood is reversed and it flows downwardly to the bottom sealing in the second section, thus co-current with the gas flow. The blood leaves the chamber at the blood outlet. By this arrangement the blood path through the chamber is approximately doubled. Furthermore, the blood flow is not only co-current or counter-current with the gas flow but counter-current and co-current with the gas flow. This leads to an enhanced gas exchange rate between blood and gas.

Further partitioning walls being sealed in the bottom sealing or top sealing may be arranged inside the chamber to further enlarge the flow path of the blood and enhance the gas exchange rate. In connection with the partitioning wall the annular chamber may be filled with the hollow fiber filaments in an arrangement wherein the fibers of the first plurality of fibers have an inclination angle with the longitudinal axis of the core of less than 90° and the fibers of the second plurality of fibers have an inclination angle with the longitudinal axis of the core of between 0° and the inclination angle of the fibers of the first plurality of fibers, preferably 10° to 25° and 0° to 7°, respectively.

Best results are obtained when the fibers are arranged in the latter manner, especially at angles of 4° and 12°, respectively.

Heat Exchanger

Optionally the blood inlet of the hollow fiber oxygenator according to the present invention may be provided with a heat exchanger for controlling the temperature of the incoming blood. According to the preferred embodiments depicted in FIGS. 1 to 3 the heat exchanger is located in the bottom of the oxygenator inside the core of the oxygenator and comprises a plurality of metal tubes 80 in which a heat exchanging fluid is circulated. The blood is passed along the outsides of the metal tubes 80 which are spaced from each other. The fluid used to control the temperature inside the heat exchanger is preferably water.

Method for Oxygenating Blood

According to the present invention a method for oxygenating blood is provided, comprising passing a free oxygen containing gas through a plurality of hollow fiber filaments extending principally axially through an oxygenator chamber and passing blood through the oxygenator chamber, wherein the blood flows primarily axially through the chamber along the plurality of fibers, characterized in that the fibers are arranged in such a way that they cause integrally a helical flow of the blood around the axis of the chamber.

According to a second embodiment of the present invention a method for oxygenating blood is provided, comprising passing a free oxygen containing gas through a plurality of hollow fiber filaments extending principally axially through an oxygenator chamber and passing blood through the oxygenator chamber, wherein blood flows primarily axially through the chamber along the plurality of fibers, characterized in that the blood in the first section of said chamber flows essentially in the opposite direction as the flow of the free oxygen containing gas through the fibers in said first section and that the blood in a second section of said chamber flows essentially in the same direction as the flow of the free oxygen containing gas through the fibers in said second section.

According to another embodiment of the present invention a method for oxygenating blood is provided, comprising passing blood via blood inlet and blood outlet through the oxygenator as described above and passing a free oxygen containing gas via the gas inlet and gas outlet through the oxygenator, and optionally controlling the temperature of the blood, in particular with the proviso that the method is not used for therapeutical treatment of the human or animal body.

Operating Conditions

The gas used in the hollow fiber oxygenator according to the present invention may be any gas containing free oxygen which is apt to transfer oxygen through the semipermeable hollow fibers into the blood and to receive carbon dioxide from the blood. Preferably, the gas should have a free oxygen content of from 21 to 100 vol. %, preferably from 60 to 90 vol. %. The preferred gas is air, which has an oxygen content of 21%, preferably mixed with a second free oxygen containing gas, so that the preferred oxygen content of from 60 to 90 vol. % is obtained. The gas pressure difference applied at the gas inlet and gas outlet may be from 0 to 13.3 kPa, preferably from 0 to 4 kPa. This results in a gas flow of from 0.2 to 10 l/min. for a preferred embodiment of the oxygenator according to the present invention as depicted in FIGS. 1 to 3.

To be useful in a cardiopulmonary bloodstream circulation of a human body the blood flow through the oxygenator must be in the range of from 1 to 6 l/min. In the blood oxygenator according to the present invention the blood flow may be arranged from 0.2 to 6 l/min., preferably from 1 to 6 l/min. To effect this blood flow a pressure difference of from 8 to 27 kPa must be applied between the blood inlet and the blood outlet. With a blood flow of 6 l/min. the typical residence time of the blood inside the hollow fiber oxygenator according to the present invention is 1/6 min. The flow path of the blood along the hollow fibers is approximately 180 mm. Details of the blood flow path can be seen in FIG. S. Without being bound to any theory it is believed that the blood flows along the hollow filament fibers helically around the axis of the chamber. This ensures an effective contact of the blood with the outer surface of the hollow fibers resulting in an improved oxygen exchange.

In comparison to the known blood oxygenators the hollow fiber blood oxygenator according to the present invention exhibits a high gas exchange rate while having a small size of the chamber filled with hollow filament fibers. No channeling of blood is observed in the oxygenator according to the present invention nor are areas of blood stagnation observed. The pressure drop of the blood flowing through the oxygenator is low.

The following examples demonstrate the advantages of the hollow fiber oxygenator according to the present invention with regard to the preferred embodiments.

EXAMPLE 1

A hollow fiber blood oxygenator according to FIG. 1 was assembled by using 3.2 up to 3.6 $m^2$ of the hollow filament fibers manufactured by AKZO ENKA GROUP to fill the annular chamber between the core wall and the outer wall. One half of the filaments were arranged with an inclination angle of 4° with respect to the longitudinal axis of the core and the other half of the fibers were arranged around the core with an inclination angle of 12° with respect to the longitudinal axis of the core. This corresponds to circumferential angle difference of 8° and 25°, respectively. Two strips of fibers each having one of the different inclination angles were arranged in the chamber. The blood oxygenator was used to treat the blood coming from a patient in an extracorporeal circulation having an initial oxygen content of 11 ml/dl and an initial carbon dioxide content of 55 ml/dl. The applied blood pressure difference was 26.6 kPa and the applied pressure difference for the air was 4 kPa. Thus, flow rates for the gas were 6 l/min. and 6 l/min. for the blood. The blood leaving the oxygenator had an oxygen content of 19.3 ml/dl and a carbon dioxide content of 50 ml/dl. Thus, the blood oxygenator according to the present invention showed a superior gas exchange rate. No stagnation or channeling of blood and no agglomeration of blood particles was observed.

EXAMPLE 2

A hollow fiber blood oxygenator was arranged according to FIGS. 2 and 3 by using hollow filament fiber, manufactured by the AKZO ENKA GROUP. The annular chamber was filled with the fibers by cross winding. Further experimental conditions were as follows:

A partitioning wall made of polypropylene was inserted in the annular chamber equally spaced to the outer wall at a distance of 7–8 mm. The partitioning wall was sealed in the bottom sealing of the chamber. It extended parallel to the outer and core wall and terminated at a distance of 13–15 mm from the top sealing.

The blood oxygenator according to example 2 showed a high gas exchange rate. No channeling or stagnation of blood was observed.

EXAMPLE 3

A hollow fiber blood oxygenator was arranged according to FIGS. 2 and 3 by using hollow filament fiber, manufactured by the AKZO ENKA GROUP. The annular chamber was filled with the fibers by the same method as applied in example 1. Further experimental conditions were as follows:

A partitioning wall made of polypropylene was inserted in the annular chamber equally spaced to the outer wall at a distance of 7–8 mm. The partitioning wall was sealed in the bottom sealing of the chamber. It extended parallel to the outer and core wall and terminated at a distance of 13–15 mm from the top sealing.

The blood oxygenator according to example 3 showed a high gas exchange rate. No channeling or stagnation of blood was observed.

EXAMPLE 4

Comparative Example

A commercially available hollow fiber blood oxygenator (DIDECO 7003 ITALIAN COMPANY) was used in a comparative experiment. Experimental conditions were as follows:

| | | |
|---|---|---|
| Blood in: | $CO_2$ content = | 60 ml/dl |
| | $O_2$ content = | 11.2 ml/dl |
| Blood out: | $CO_2$ content = | 54 ml/dl |
| | $O_2$ content = | 17.6 ml/dl |

The pressure drop for the blood was 22.6 kPa. The flow rate for the gas was 6 l/min. and the flow rate for the blood was 6 l/min.

The results from Examples 1, 2 and 3 and comparative Example 4 show that the specific arrangement of hollow fiber filaments inside the hollow fiber blood oxygenator according to the present invention results in an improvement of gas exchange rate, while preventing channeling or stagnation of blood.

I claim:

1. A hollow fiber oxygenator, comprising:
   a housing defining a blood flow chamber therein, wherin the housing is defined by an outer wall and an inner core wall, and wherein the chamber is formed therebetween;
   a plurality of selectively permeable hollow fibers extending in the chamber, each fiber having an open gas inlet end and an open gas outlet end, the inlet and outlet ends of the fibers being respectively sealed from fluid communication with the chamber;
   a gas inlet to the inlet ends of the fibers;
   a gas outlet from the outlet ends of the fibers, wherein gas may flow within each hollow fiber from the inlet end to the outlet end thereof;
   a blood inlet to the chamber;

a blood outlet from the chamber, wherein blood may flow through the chamber from the blood inlet to the blood outlet and contact the exterior surfaces of the selectively permeable fibers, the fibers enabling gas transfer between the gas flowing within the fibers and the blood flowing in the chamber; and a partition wall in the chamber dividing the chamber into at least two sections with hollow fibers extending in each section, the sections defining a blood flow path from the blood inlet to the blood outlet, wherein in at least one section the blood flow direction along the blood flow path is counter-current with respect to the gas flow within the hollow fibers in that section, and in at least one other section the blood flow direction along the blood flow path is co-current with respect to the gas flow within the hollow fibers in that section.

2. The oxygenator of claim 1, wherein there are only two sections formed within the chamber having approximately the same volume.

3. The oxygenator of claim 1, further including a heat exchanging device attached to the housing for modifying the temperature of the blood.

4. The oxygenator of claim 1, wherein the chamber is annularly formed between the outer wall and the inner core wall of the housing.

5. The oxygenator of claim 4, further including a heat exchanging device attached to the housing for modifying the temperature of the blood wherein the heat exchanger is positioned partly within the core wall at one axial end thereof, and includes a blood inlet port, and a blood outlet port in communication with the blood inlet to the chamber.

6. The oxygenator of claim 4, wherein both the blood inlet and the blood outlet are located at a first axial end of the annular chamber.

7. The oxygenator of claim 6, wherein the partition wall is positioned in the chamber between the outer wall and core wall.

8. The oxygenator of claim 7, wherein the partition wall is generally tubular and extends axially in the annular chamber from the first axial end toward a second axial end opposite the first axial end, wherein only two of the sections are formed in the chamber, a first section on one radial side of the partition wall and a second section on the other radial side, and wherein a flow connection distal from the first axial end of the chamber is defined by the partition wall so that blood flows from the blood inlet through the first section, through the flow connection, and then through the second section to the blood outlet.

9. The oxygenator of claim 8, wherein the gas inlet is disposed at the second axial end of the chamber and the gas outlet is disposed at the first axial end so that gas flows axially within the fibers from the second end to the first end, counter-current to the blood flow path in the first section and co-current to the blood flow path in the second section.

10. The oxygenator of claim 9, further including a first sealing at the first end of the chamber closing the chamber from the gas outlet, and a second sealing at the second axial end of the chamber closing the chamber from the gas inlet, wherein the partition wall is in contact with the first sealing.

11. The oxygenator of claim 10, wherein the partition extends all the way to the second sealing and include apertures proximate the second sealing defining the flow connection.

12. The oxygenator of claim 10, wherein the partition wall stops short of the second sealing and defines a gap therebetween, thus forming the flow connection.

13. The oxygenator of claim 8, wherein the blood inlet comprises apertures formed in the core wall, and the blood outlet comprises apertures formed in the outer wall, wherein the first section of the chamber is concentrically located within the second section, with the partition wall therebetween.

14. The oxygenator of claim 8, wherein the partition wall is spaced from the outer wall and the core wall, respectively, so as to form two sections within the chamber having approximately the same volume.

15. The oxygenator of claim 1, wherein the plurality of selectively permeable hollow fibers comprises successive layers of fibers, each layer of fibers comprising a plurality of fibers aligned in parallel and connected together to form a mat, the fibers in each layer being oriented to form an angle with the fibers in each adjacent layer.

16. The oxygenator of claim 14, wherein the chamber is annular and each fiber extends helically between a first axial end and a second axial end thereof with a circumferential angle difference of less than, or equal to 180°.

17. The oxygenator of claim 16, wherein the circumferential angle difference of each fiber is less than or equal to 90°.

18. The oxygenator of claim 14, wherein the fibers in adjacent layers are wound helically within the chamber in the same rotational sense.

19. The oxygenator of claim 14, wherein the fibers in adjacent layers have inclination angles within 40° of each other.

20. The oxygenator of claim 1, wherein the chamber extends generally longitudinally with a first end and a second end and wherein both the blood inlet and the blood outlet are located at the first end of the chamber.

21. The oxygenator of claim 20, wherein the partition wall extends longitudinally in the chamber from the first end toward the second end, wherein only two of the sections are formed in the chamber, a first section on one side of the partition wall and a second section on the other side surrounding the first side, and wherein a flow connection distal from the first end of the chamber is defined by the partition wall so that blood flows from the blood inlet through the first section, through the flow connection, and then through the second section to the blood outlet.

22. The oxygenator of claim 21, wherein the gas inlet is disposed at the second end of the chamber and the gas outlet is disposed at the first end so that gas flows within the fibers from the second end to the first end, counter-current to the blood flow path in the first section and co-current to the blood flow path in the second section.

23. The oxygenator of claim 22, further including a first sealing at the first end of the chamber closing the chamber from the gas outlet, and a second sealing at the second end of the chamber closing the chamber from the gas inlet, wherein the partition wall is in contact with the first sealing.

24. A method for oxygenating blood, comprising:

passing a free oxygen containing gas through a plurality of hollow fibers extending through an oxygenator chamber, wherein the chamber is formed between an outer housing wall and an inner housing core wall;

passing blood through a first section of the chamber into contact with fibers in that section; and passing the blood which flowed through the first section of the chamber through a second section of the chamber into contact with fibers in that section, wherein blood flows co-current with respect to the flow of oxygen containing gas within the fibers in one of the sections and counter-current with respect to the flow of oxygen containing gas within the fibers in the other of the sections.

25. The method of claim 24, wherein the chamber is annularly formed between the outer housing wall and the inner housing core wall, and the housing includes a blood inlet and a blood outlet in communication with the annular chamber at one axial end thereof, and a generally tubular partition wall extending axially in the annular chamber from a first axial end toward a second axial end opposite the first axial end, wherein the first section is defined on one radial side of the partition wall and a second section on the other radial side, and wherein a flow connection distal from the first axial end of the chamber is defined by the partition wall, the method further comprising:

flowing blood from the blood inlet through the first section in a first axial direction, through the flow connection, and then through the second section in a second axial direction opposite the first to the blood outlet.

26. The method of claim 25, further including:

flowing gas axially within the fibers from the second end to the first end so that blood flows counter-current to the gas flow in the first section and co-current to the gas flow in the second section.

27. The method of claim 25, wherein the first section is radially inward from the partition wall, the method further comprising:

i) flowing blood from the first section outwardly through the flow connection into the second section.

28. The method of claim 24, wherein the oxygenator includes a heat exchanger attached thereto, the method further comprising:

heating the blood.

29. The method of claim 24, wherein the housing extends generally longitudinally with a first end and a second end and includes a blood inlet and a blood outlet in communication with the chamber at one end thereof, the oxygenator also having a partition wall extending longitudinally in the chamber from the first end toward the second end, wherein the first section is defined on one side of the partition wall and the second section is defined on the other side of the partition wall and surrounding the first section, and wherein a flow connection distal from the first end of the chamber is defined by the partition wall, the method further comprising:

flowing blood from the blood inlet through the first section in a first direction, through the flow connection, and then through the second section in a second direction opposite the first to the blood outlet.

* * * * *